US007713551B2

(12) United States Patent
McGurk et al.

(10) Patent No.: US 7,713,551 B2
(45) Date of Patent: May 11, 2010

(54) GEL STABILIZED NANOPARTICULATE ACTIVE AGENT COMPOSITIONS

(75) Inventors: Simon L. McGurk, King of Prussia, PA (US); David A. Czekai, Spring City, PA (US)

(73) Assignee: Elan Pharma International Ltd., Athlone, County Westmeath (IE)

( * ) Notice: Subject to any disclaimer, the term of this patent is extended or adjusted under 35 U.S.C. 154(b) by 428 days.

(21) Appl. No.: 10/659,706

(22) Filed: Sep. 11, 2003

(65) Prior Publication Data

US 2005/0031691 A1 Feb. 10, 2005

Related U.S. Application Data

(60) Provisional application No. 60/409,587, filed on Sep. 11, 2002.

(51) Int. Cl.
*A61K 9/14* (2006.01)

(52) U.S. Cl. .................. 424/484; 424/485; 424/486; 424/489; 424/492

(58) Field of Classification Search ................. None
See application file for complete search history.

(56) References Cited

U.S. PATENT DOCUMENTS

| 4,003,999 | A | * | 1/1977 | Lybrand et al. ............. 424/729 |
| 4,486,412 | A | | 12/1984 | Shah et al. |
| 4,708,834 | A | | 11/1987 | Cohen et al. |
| 4,783,484 | A | | 11/1988 | Violante et al. |
| 4,795,642 | A | | 1/1989 | Cohen et al. |
| 4,826,689 | A | | 5/1989 | Violanto et al. |
| 4,837,255 | A | * | 6/1989 | Dechow ..................... 524/23 |
| 4,882,157 | A | * | 11/1989 | Yang et al. ................. 424/440 |
| 4,935,243 | A | | 6/1990 | Borkan et al. |
| 4,997,454 | A | | 3/1991 | Violante et al. |
| 5,145,684 | A | * | 9/1992 | Liversidge et al. ......... 424/489 |
| 5,146,730 | A | | 9/1992 | Sadek et al. |
| 5,200,191 | A | | 4/1993 | Steele et al. |
| 5,298,262 | A | | 3/1994 | Na et al. |
| 5,302,401 | A | | 4/1994 | Liversidge et al. |
| 5,318,767 | A | | 6/1994 | Liversidge et al. |
| 5,326,552 | A | | 7/1994 | Na et al. |

(Continued)

FOREIGN PATENT DOCUMENTS

EP 0719549 * 3/1996

(Continued)

OTHER PUBLICATIONS

Sadar, M., "Turbidity Science," *Technical Information Series*, Booklet No. 11, pp. 4-26, 1998.

(Continued)

*Primary Examiner*—Eric E. Silverman
(74) *Attorney, Agent, or Firm*—Foley & Lardner LLP

(57) ABSTRACT

Disclosed is a solid or semi-solid gelatin nanoparticulate active agent dosage form comprising at least one nanoparticulate active agent and at least one gel forming substance which exhibits gelation sufficient to retain excess water in the solid or semi-solid gelatin form. The active agent particles have an effective average diameter prior to inclusion in the dosage form of less than about 2000 nm. The dosage form of the invention has the advantages of easy administration combined with rapid dissolution of the active agent following administration.

44 Claims, 5 Drawing Sheets

U.S. PATENT DOCUMENTS

| | | |
|---|---|---|
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,459,983 A | 10/1995 | Sadek et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,718,388 A | 2/1998 | Czekai et al. |
| 5,718,919 A | 2/1998 | Ruddy et al. |
| 5,741,522 A | 4/1998 | Violante et al. |
| 5,776,496 A | 7/1998 | Violante et al. |
| 5,834,025 A | 11/1998 | De Garavilla et al. |
| 5,862,999 A | 1/1999 | Czekai et al. |
| 5,932,245 A | 8/1999 | Wunderlich et al. |
| 6,045,829 A | 4/2000 | Liversidge et al. |
| 6,066,332 A | 5/2000 | Wunderlich et al. |
| 6,068,858 A | 5/2000 | Liversidge et al. |
| 6,153,225 A | 11/2000 | Lee et al. |
| 6,165,506 A | 12/2000 | Jain et al. |
| 6,183,845 B1 | 2/2001 | Ikemoto |
| 6,197,787 B1 | 3/2001 | Franson et al. |
| 6,217,902 B1 | 4/2001 | Tanner et al. |
| 6,221,400 B1 | 4/2001 | Liversidge et al. |
| 6,251,426 B1 | 6/2001 | Gullapalli |
| 6,258,380 B1 | 7/2001 | Overholt |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 * | 11/2001 | Jain et al. ............... 424/484 |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,482,516 B1 | 11/2002 | Sadek et al. |
| 6,582,285 B2 | 6/2003 | Czekai et al. |
| 6,592,903 B2 | 7/2003 | Ryde et al. |
| 6,685,961 B1 | 2/2004 | Gennadios et al. |
| 6,949,256 B2 | 9/2005 | Fonkwe et al. |
| RE39,347 E | 10/2006 | Ikemoto |
| 2002/0012675 A1 | 1/2002 | Jain et al. |
| 2006/0088590 A1 | 4/2006 | Sukuru et al. |
| 2007/0098783 A1 | 5/2007 | Sukuru |
| 2007/0148248 A1 | 6/2007 | Chidambaram |

FOREIGN PATENT DOCUMENTS

| | | | |
|---|---|---|---|
| EP | 0 950 402 B1 | | 10/1999 |
| WO | WO 00/18374 | * | 4/2000 |
| WO | WO 00/18374 A1 | | 4/2000 |
| WO | WO 02/098565 A1 | | 12/2002 |
| WO | WO 2004/030648 A1 | | 4/2004 |

OTHER PUBLICATIONS

Rowe, R, et al (eds), "Gelatin," *Handbook of Pharmaceutical Excipients,* Fourth Edition, pp. 252-254, 2001.

Lindahl et al., "Characterization of Fluids from the Stomach and Proximal Jejunum in Men and Women," *Pharm. Res.,* 14(4): 497-502 (1997).

* cited by examiner

GEL STABILIZED NANOPARTICULATE ACTIVE AGENT COMPOSITIONS

FIELD OF THE INVENTION

The present invention relates to a solid or semi-solid gelatin dosage formulation comprising a nanoparticulate active agent. Prior to incorporation in the dosage form, the nanoparticulate active agent preferably has an effective average particle size of less than about 2 microns.

BACKGROUND OF THE INVENTION

A. Background Related to Nanoparticulate Compositions

Nanoparticulate active agent compositions, first described in U.S. Pat. No. 5,145,684 ("the '684 patent"), are particles consisting of a poorly soluble active agent having adsorbed onto or associated with the surface thereof a non-crosslinked surface stabilizer. The '684 patent also describes methods of making such nanoparticulate active agent compositions. Nanoparticulate compositions are desirable because with a decrease in particle size, and a consequent increase in surface area, a composition is rapidly dissolved and absorbed following administration.

Methods of making nanoparticulate active agent compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract;" U.S. Pat. No. 6,582,285 for "Apparatus for Sanitary Wet Milling;" and U.S. Pat. No. 6,592,903 for "Nanoparticulate Dispersions Comprising a Synergistic Combination of a Polymeric Surface Stabilizer and Dioctyl Sodium Sulfosuccinate;" all of which are specifically incorporated by reference. In addition, U.S. Patent Application No. 20020012675 A1, published on Jan. 31, 2002, for "Controlled Release Nanoparticulate Compositions," and International Application No. WO 02/098565, published on Dec. 12, 2002, describe nanoparticulate active agent compositions, and are specifically incorporated by reference.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter." None of these references, or any other reference that describes nanoparticulate compositions, relates to a rapidly dissolving solid or semi-solid gelatin dosage form comprising a nanoparticulate active agent.

B. Background Related to Dosage Formulations

Drug products are currently designed for three groups of individuals: infants, pediatrics, and adults. The needs of infants are different from those of children 2 to 12 years of age, and the needs of children are different from those of adults. Moreover, the needs of the elderly population are different than those of other adults. Another category of individuals needing an alternative drug delivery form are patients with chronic dosage regimens. Repeated dosing of tablets or pills may become problematic for patients having a need for daily dosage regimens. Thus, an alternative dosage form is needed for a variety of patient populations.

Pediatric patients have difficulty swallowing until they reach the age of about 10-16 years old. Younger pediatric patients generally take either chewable tablets, crush and mix regular tablets with food/juice, or take a liquid dosage form. Chewable tablets, generally a good dosage form, do not always sufficiently mask the taste of the active agent. Crushing and mixing regular tablets with food or juice is time-consuming, messy, and not always practical. The difficulty of liquid dosage forms, e.g., syrups, is that they are bulky, do not always taste good, and can be unstable as compared to a solid dosage form, such as a tablet. A practical and new dosage form would be of value for these patients.

With advancements in medical science and the focus on healthy lifestyles, there is projected growth of the elderly population in the U.S. and abroad. Currently, the U.S. population of persons 65 years of age or older receives nearly 30% of the medications prescribed. Moreover, it is anticipated that there may be a rise in the demand for drugs by the elderly. In spite of the disproportionately large demand for prescription pharmaceuticals among the elderly, relatively little attention has been directed to meeting the unique pharmacotherapeutic needs of this age group.

Many older patients experience difficulty in swallowing tablets or capsules and yet the vast majority of dosage forms administered to the elderly are tablets or capsules. Uncoated tablets are convenient and economical to manufacture but are often difficult to swallow and frequently cause discomfort by "hanging" in the throat. Coated tablets and capsules are somewhat easier to swallow but with increasing age and the large number of drug products that are administered to a single individual, this is a source of apprehension. Liquid dosage forms are relatively easy to administer but are more costly, easily spilled, often do not taste good, occupy large volumes of space per dosage unit, and possess stability problems.

As is evident, the needs of the elderly differ from those of other populations and deserve special attention in new drug development, product formulation, product packaging, product labeling, patient information, and product marketing and sales. A practical and new dosage form would be of value for these patients as well as others.

C. Background Related to Gelatin Dosage Forms

A gelatin drug delivery system would be beneficial in achieving ease of administration in both young, older, and chronic dosage patients. However, such a dosage system must exhibit sufficient stability and bioavailability. Without sufficient bioavailability and active agent stability, ease of administration is just a single step in the process of pharmaceutical therapy. Prior art gelatin dosage forms have been unable to solve this dual necessity of bioavailability in combination with active agent stability.

The most typical gelatin drug delivery formulations comprise gelatin coated tablet formulations and gelatin encapsulated solid cores or liquid cores of pharmaceutical agents. One such example is found in U.S. Pat. No. 6,197,787 to Franson et al., which discloses a concentrated drug solution for a soft gelatin capsule filling consisting essentially of: (a) a poorly soluble organic acid drug, such an analgesic, anti-inflammatory agent, anthelmintic, etc.; (b) propylene glycol; (c) sodium hydroxide; and (d) water. However, this dosage formulation is a gelatin capsule and not a solid or semi-solid gelatin formulation.

Another example of a soft gelatin capsule is found in U.S. Pat. No. 6,217,902 to Tanner et al. Tanner et al. disclose a soft gelatin capsule comprising a suspension of a solid phase in a liquid phase, with the solid phase consisting of encapsulated beads having a mean diameter of from about 149 µm to 2500 µm. The beads comprise a coating effective to prevent interaction of the active agent with the liquid phase or the soft gelatin capsule. Tanner et al. fail to disclose a solid or semi-solid gelatin formulation.

An example of a gelatin dosage form has been disclosed by Wunderlich in U.S. Pat. No. 5,932,245 ("the '245 patent"). This patent is directed to a dosage formulation that provides: (a) an inner phase comprising at least one nanoparticle compound having an average size ranging from 10 to 800 nanometers; and (b) an outer phase comprising gelatin, collagen hydrolyzates, or mixtures thereof. The inner phase of this composition is negatively charged and the outer phase is positively charged when the dosage formulation is dissolved in an aqueous solution having a pH of less than 9.5, or the inner phase is positively charged and the outer phase is negatively charged when the dosage formulation is dissolved in an aqueous solution having a pH of higher than 3.5.

This reference differs from the present invention in several aspects. First, the '245 patent requires solubilization of the active agent as part of the process of making the described nanosol compositions. The solubilization is achieved either through the use of a solvent (col. 17, lines 30-34), followed by evaporation of the solvent, or through modification of the pH of the gelatin. For example, an active agent is dissolved in ethanol, isopropanol, methanol, or acetone (col. 18, lines 32-36; col. 20, lines 18-20 and 44-48; col. 22, lines 4-5 and 29; col. 23, lines 30-32) or the active agent is dissolved in the gelatin via modifying the pH of the gelatin (col. 18, lines 52-55; col. 21, lines 23-28 and 43-50; col. 22, lines 61-67). Such solubilization of an active agent is undesirable, as solubilization affects the various properties of the active agent, such as the solidification state of the active agent (i.e., whether the active agent is in an amorphous or crystalline form), stability of the active agent in the aqueous state, how much of the active agent has returned to the solid state, etc. Such solubilization is required because in the compositions of the '245 patent, the gelatin functions to stabilize the nanoparticles of the active agent, as pictured in FIG. 5.

The only way to have the gelatin composition "surround and stabilize" the active agent in the composition of the '245 patent is to first solubilize the active agent in the gelatin, or in a solvent followed by mixing the solvent/active agent solution with the gelatin solution and subsequent evaporation of the solvent.

This is in contrast to traditional nanoparticulate drugs, which do not require solubilization of the active agent. Rather, such compositions utilize a surface stabilizer, such as a surfactant, to stabilize the nanoparticulate size of the active agent following particle size reduction via, for example, milling or homogenization. See e.g., U.S. Pat. No. 5,145,684 for "Surface Modified Nanoparticulate Drugs." However, the '245 patent teaches that the use of surfactants is undesirable in the disclosed compositions because such surfactants can have side effects and possible toxicity. See col. 4, lines 12-14.

Finally, another drawback to the formulation of the '245 patent is that it does not retain excess water, which is essential for effective redispersability, and hence this dosage form may exhibit poor pharmaceutical bioavailability. This is likely because the gelatin formulation of the '245 patent is not a hydrated gelatin.

Similarly, U.S. Pat. No. 6,066,332 ("the '332 patent") to Wunderlich et al. describes a gelatin dosage form containing ibuprofen, having a particle size of from 10 to 800 nanometers, in the form of a nanosol. As with the compositions of the '245 patent, the '332 patent requires solubilization of ibuprofen to make the described gelatin formulations. See e.g., col. 8, line 60, through col. 9, line 5; col. 9, lines 15-16 and 31-34. The ibuprofen is dissolved in a solvent such as ethanol, isopropanol, methanol, or acetone (col. 8, lines 60-62; col. 9, lines 31-34; col. 16, lines 13-15), or the ibuprofen is dissolved in the gelatin via modifying the pH of the gelatin (col. 9, lines 10-16; col. 15, lines 28-35). Such solubilization of an active agent such as ibuprofen is undesirable, as described above.

Moreover, as with the '245 patent, another drawback to the formulation of the '332 patent is that it does not retain excess water, which is essential for effective redispersability, and hence this dosage form may exhibit poor pharmaceutical bioavailability.

Another example of a gelatin dosage form is disclosed by Allen et al. in U.S. Pat. No. 6,066,337. This patent is directed to a rapidly dissolving pharmaceutical dosage form produced by combining a particulate support matrix with a pharmaceutical ingredient to form a dosage mixture, followed by forming the dosage mixture into a dosage form. When introduced into an aqueous environment, the dosage form is substantially completely disintegrable within less than about 20 seconds. The particulate support matrix is formed by providing an aqueous composition comprising: (a) an aqueous medium, (b) a support agent comprising a non-hydrolyzed gelatin component having a predetermined net charge, (c) a hydrolyzed gelatin component having a predetermined net charge of the same sign as the non-hydrolyzed gelatin component, (d) a bulking agent, and (e) a volatilizing agent. The hydrolyzed gelatin component has a solubility in aqueous solution greater than that of the non-hydrolyzed component. The aqueous composition is introduced as droplets into a drying chamber heated to a temperature sufficient to cause evaporation of substantially all of the aqueous medium and volatilizing agent from the droplets leaving the support agent in a dried particulate form comprising the particulate support matrix. This formulation fails to retain excess water, which is essential for effective redispersability, and hence the Allen et al. formulation exhibits poor pharmaceutical bioavailability.

None of the described prior art teaches a rapidly disintegrating gelatin-based solid or semi-solid dosage form in which an active and stable ingredient is in a nanoparticulate form, which does not require solubilization of the active agent as part of the process of making the dosage form, and wherein the gel-forming substance retains excess water, thereby providing sufficient pharmaceutical bioavailability. This is significant because the prior art gelatin drug delivery systems fail to retain water in the gel matrix, which therefore inhibits or prevents redispersability, and hence the prior art gelatin formulations exhibit poor pharmaceutical bioavailability. Moreover, prior art gelatin dosage forms required solubilization of component active agents, which is undesirable as solubilization of an active agent can change the active agent's pharmacological and pharmacokinetic characteristics.

There is a need in the art for drug dosage forms having ease of administration, active agent stability, and increased pharmaceutical bioavailability for active agents. The present invention satisfies these needs.

SUMMARY OF THE INVENTION

This invention is directed to the surprising and unexpected discovery of new gelatin solid or semi-solid dose formulations of nanoparticulate active agents. The new dosage forms comprise a gel-forming substance which exhibits gelation sufficient to retain excess water in the solid or semi-solid gel.

The gelatin solid or semi-solid dose formulations of nanoparticulate active agent compositions comprise at least one nanoparticulate active agent having an effective average particle size of less than about 2000 nm, and at least one surface stabilizer adsorbed on or associated with the surface thereof. The active agent can be poorly soluble in at least one liquid media, such as water. Alternatively, if a nanoparticulate active agent is not poorly soluble, it can be conjugated to a salt or other substance to render the active agent poorly soluble. Thus, agents useful in therapeutic, cosmetic, diagnostic, bioengineering, food, or dietary supplement applications are presumed suitable for the invention.

In addition, the gelatin solid or semi-solid dose nanoparticulate active agent formulations comprise at least one gel forming substance, which provides an active agent dosage form having ease of administration, improved stability of the active agent, and improved dissolution. The gelatin solid or semi-solid dose formulation also exhibits increased redispersion of the component active agent, which achieves pharmaceutically acceptable bioavailability.

Another aspect of the invention is directed to pharmaceutical compositions comprising a nanoparticulate active agent composition of the invention. The pharmaceutical compositions preferably comprise at least one active agent, at least one surface stabilizer, at least one gel forming substance, and at least one pharmaceutically acceptable carrier, as well as any desired excipients.

In another aspect of the invention there is provided a method of preparing gelatin nanoparticulate solid or semi-solid dose formulations. The method comprises: (1) forming a nanoparticulate active agent composition comprising at least one active agent and at least one surface stabilizer; (2) mixing the nanoparticulate active agent composition with melted gelatin, and (3) forming a solid dose form of the composition for administration. The method does not comprise solubilizing the active agent. Additional pharmaceutically acceptable excipients can also be added to the composition for administration.

Yet another aspect of the present invention provides a method of treating a subject, including a human, comprising administering a solid or semi-solid gelatin nanoparticulate active agent formulation of the invention, wherein the gelatin formulation exhibits gelation sufficient to retain excess water.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1:
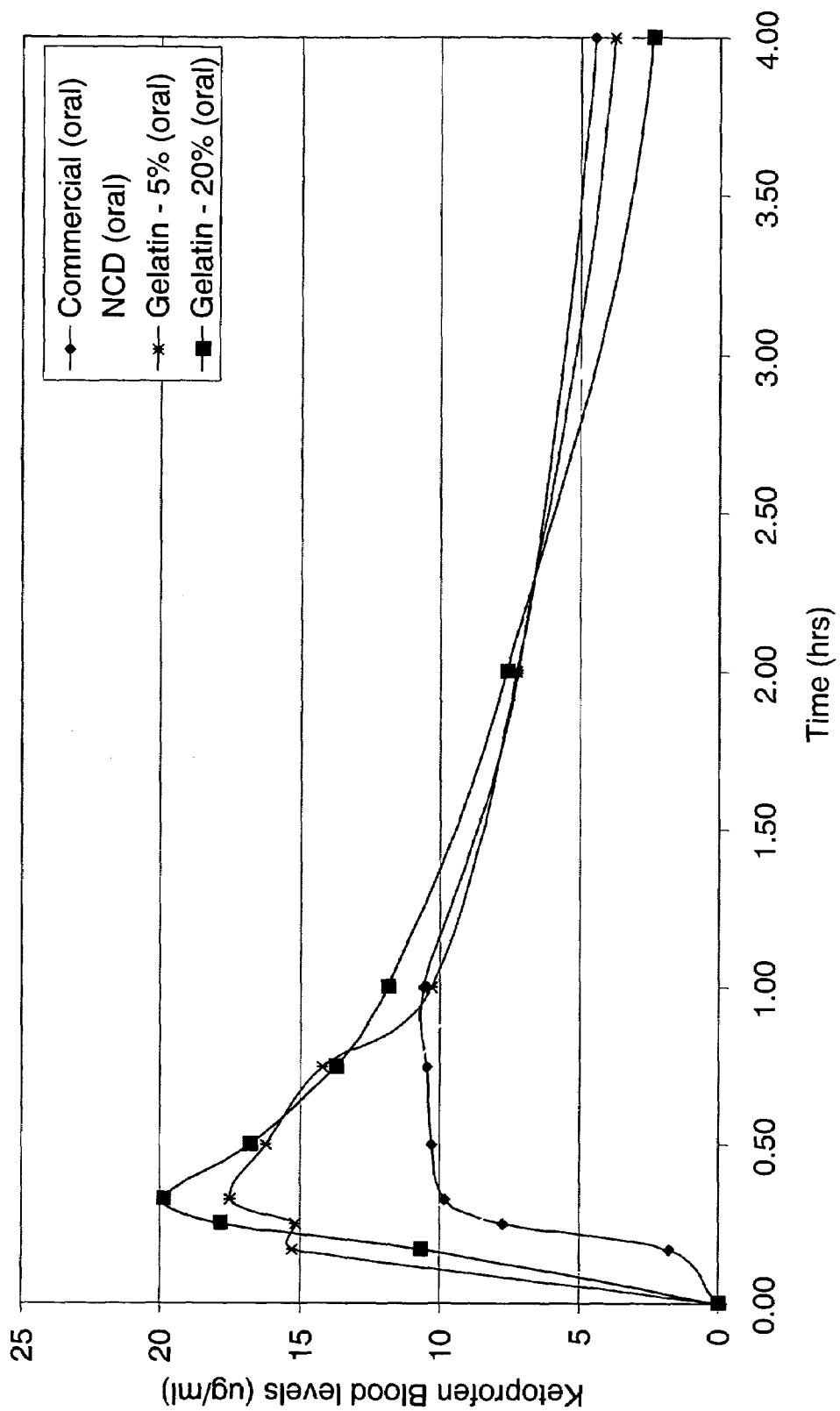
FIG. 1: Shows the blood levels of ketoprofen over a 4 hour time period following oral administration of four different 50 mg ketoprofen dosage formulations: (a) a 5% nanoparticulate ketoprofen oral gelatin formulation; (b) a 20% nanoparticulate ketoprofen oral gelatin formulation; (c) a nanoparticulate ketoprofen liquid dispersion formulation; and (d) a commercial dose of conventional ketoprofen (generic ketoprofen 50 mg capsules manufactured by Lederle Laboratories (a Division of American Cyanamid Co., Pearl River, N.Y.)). The surface stabilizers in formulations (a)-(c) are polyvinylpyrrolidone (PVP) k29/32 and sodium lauryl sulfate (SLS).

This invention is directed to the surprising and unexpected discovery of a new solid or semi-solid gelatin dosage form.

The solid or semi-solid gelatin nanoparticulate active agent formulations of the invention comprise at least one nanoparticulate active agent to be administered having an effective average particle size prior to inclusion in the dosage form of less than about 2000 nm, at least one surface stabilizer adsorbed on or associated with the surface of the active agent, and at least one gel forming substance which exhibits gelation sufficient to retain excess water in a solid or semi-solid form, thereby achieving redisperability of the active agent. Such redispersibility can result in improved bioavailability of the active agent.

Prior to the present invention, while gelatin dosage forms were desirable, there was an inherent conflict in desiring more water in the dosage form to increase redispersion of the active agent, and knowing that the presence of a significant percentage of water can result in degradation of the active agent to be delivered. It was unexpectedly discovered that the presence of water does not destabilize or degrade the nanoparticulate active agent in the dosage forms of the invention.

The gelatin dosage forms of the present invention, which retain excess water, disperse and essentially melt upon administration. The amount of water retained by the gel formulation of the invention is at least the amount required to provide for redispersability of the nanoparticulate active agent particles upon administration. This equates to a water content of from about 5% to about 97%, from about 20% to about 95%, from about 30% to about 92%, from about 45% to about 90%, or from about 65% to about 85%, based on the total weight of the composition.

Benefits of the gelatin dosage form of the invention can include, but are not limited to: (1) rapid delivery of the active agent, which can correlate with rapid active agent absorption; (2) stability of the active agent, which can include particle size and chemical stability of the active agent; (3) excellent redispersability of the active agent upon administration or in a biorelevant media; (4) improved bioavailability of the active agent as compared to a microparticulate or solubilized form of the same active agent, administered at the same dosage; (5) a more consistent bioavailability profile for the active agent, aiding in dosage determination, due to the more consistent active agent particle sizes present in the gelatin dosage form, as compared to a microparticulate or solubilized form of the same active agent, administered at the same dosage; (6) the gelatin dosage form is easily administered, requires minimal chewing, rapidly dissolves, and essentially melts at body temperature; (7) the gelatin dosage form can be formulated to mask the unpleasant taste of an active agent; (8) the gelatin dosage form is particularly useful for infant, pediatric, and elderly patient populations, as well as other patient populations which have difficulty in swallowing pills or other solid dosage forms; (9) better patient compliance as the gelatin dosage form is easier to consume and digest as compared to conventional solid dose forms, such as tablets; (10) the gelatin dosage form of the invention does not require potentially toxic solubilizing agents for the active agent; (11) smaller dosage volume as compared to a microparticulate or solubilized form of the same active agent, administered at the same dosage; (12) higher dose loading as compared to a microparticulate or solubilized form of the same active agent, administered at the same dosage; (13) smaller doses of active agent required to obtain the same pharmacological effect as compared to a microparticulate or solubilized form of the same active agent, administered at the same dosage, which can correlate with a decrease in toxicity of the active agent; (14) improved pharmacokinetic profiles as compared to a microparticulate or solubilized form of the same active agent, administered at the same dosage; (15) substantially similar and/or bioequivalent pharmacokinetic profiles of the nanoparticulate active agent compositions when administered in the fed versus the fasted state; (16) bioadhesive gelatin dosage forms of nanoparticulate active agents; and (17) the gelatin dosage forms of the invention can also comprise microparticulate and/or solubilized active agents, in combination with the nanoparticulate active agent.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Conventional active agents or drugs" refers to non-nanoparticulate or solubilized active agents or drugs. Non-nanoparticulate active agents have an effective average particle size of greater than about 2 microns.

"Poorly soluble active agents" as used herein means those having a solubility in at least one liquid media of less than about 30 mg/ml, preferably less than about 20 mg/ml, preferably less than about 10 mg/ml, or preferably less than about 1 mg/ml, under ambient temperature. Poorly water soluble active agents tend to be eliminated from the gastrointestinal tract before being absorbed into the circulation.

As used herein with reference to stable active agent particles, "stable" includes, but is not limited to, one or more of the following parameters: (1) the active agent particles are substantially chemically stable, as measured by degradent concentrations; (2) the active agent particles do not appreciably flocculate or agglomerate due to interparticle attractive forces or otherwise increase in particle size over time; (3) the physical structure of the active agent particles is not altered over time, such as by conversion from an amorphous phase to crystalline phase; (4) where the active agent has not been subjected to a heating step at or above the melting point of the active agent in the preparation of the nanoparticles of the invention.

"Therapeutically effective amount" as used herein with respect to an active agent dosage, shall mean the dosage that provides the specific pharmacological response for which the active agent is administered in a significant number of subjects in need of such treatment. It is emphasized that 'therapeutically effective amount,' administered to a particular subject in a particular instance will not always be effective in treating the diseases described herein, even though such dosage is deemed a "therapeutically effective amount" by those skilled in the art. It is to be further understood that active agent dosages are, in particular instances, measured as oral dosages, or with reference to drug levels as measured in blood.

I. Exemplary Preferred Characteristics of the Gelatin Dosage Forms of the Invention A. Redispersibility Profiles of the Gelatin Dosage Forms The solid or semi-solid nanoparticulate active agent gelatin dosage forms of the invention exhibit gelation sufficient to retain excess water in the solid or semi-solid active agent dosage form, which provides for rapid redispersion of the active agent. Such rapid redispersion can preferably correlate with increased bioavailability of the active agent. This is significant because previous gelatin formulations failed to contain water, or sufficient amounts of water, because of stability considerations. When insufficient water is present in a gelatin dosage form, the active agent is not sufficiently dissolved and absorbed into the blood stream following administration because there is little or no redispersability of the active agent in vivo.

The solid or semi-solid nanoparticulate active agent gelatin dosage forms of the invention preferably redisperse such that the effective average particle size of the redispersed active agent particles is less than about 2 microns. This is significant, as if upon administration the nanoparticulate active agent compositions of the invention did not redisperse to a substantially nanoparticulate particle size, then the gelatin dosage form may lose the benefits afforded by formulating the active agent into a nanoparticulate particle size.

This is because nanoparticulate active agent compositions benefit from the small particle size of the active agent; if the active agent does not redisperse into the small particle sizes upon administration, then "clumps" or agglomerated active agent particles are formed, owing to the extremely high surface free energy of the nanoparticulate active agent system and the thermodynamic driving force to achieve an overall reduction in free energy. With the formation of such agglomerated particles, the bioavailability of the dosage form may fall well below that observed with a form of the nanoparticulate active agent that does not form such agglomerated particles.

Moreover, the gelatin dosage forms of the invention preferably exhibit dramatic redispersion of the component nanoparticulate active agent particles upon administration to a mammal, such as a human or animal, as demonstrated by reconstitution/redispersion in a biorelevant aqueous media such that the effective average particle size of the redispersed active agent particles is less than about 2 microns. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1 M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed active agent particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate." Exemplary redispersion media includes, but is not limited to, sterile water for injection, saline, dextrose, Lactated Ringer's solution, and Ringers solution.

B. Improved Bioavailability

An advantage typically associated with the solid or semi-solid gelatin dosage forms of the invention is a reduction of the time lag between administration of a dose and the physical presentation of the active agent. This lag time is usually associated with the break up of the dosage form and the distribution of the active agent thereafter.

A second advantage of the solid or semi-solid gelatin dosage forms is that the gelatin melts at body temperature. Thus, upon administration, the active agent may be absorbed buccally directly into the blood stream, thus reducing the first pass effect of the liver on the overall bioavailability of active agent from a unit dose. This second advantage is enhanced because the incorporation of the nanoparticulate size of the active agent into the solid or semi-solid gelatin formulations of the invention enables rapid dissolution in the oral cavity.

This combination of rapid delivery, stability, and improved redispersability preferably can achieve increased bioavailability of the active agent as compared to prior known gelatin-containing active agent delivery systems. Surprisingly, the gelatin dosage forms of the invention are also superior to nanoparticulate active agent dispersions of the same active agent. This is particularly unexpected as generally liquid dosage forms have greater bioavailability and faster onset of action as compared to solid or semi-solid dosage forms.

In addition, the gelatin dosage forms of the invention may provide a more consistent bioavailability profile, which aids in dosage determination, as the gelatin dosage forms of the invention preferably have a narrow active agent particle size range. Gelatin dosage forms having highly variable active agent particle sizes, including large crystals, can result in a variable bioavailability profile from dose to dose because smaller particles dissolve faster than the larger aggregates or larger crystal particles. For active agents having a dissolution-rate limited bioavailability, such as poorly water soluble active agents, a faster rate of dissolution is associated with greater bioavailability and a slower rate of dissolution is associated with a lower bioavailability. In such cases, bioavailability is related to the surface area of an administered active agent and, therefore, bioavailability increases with a reduction in the particle size of the dispersed agent. With a composition having widely varying particle sizes, bioavailability becomes highly variable and inconsistent and dosage determinations become difficult. This can be particularly problematic for active agents having a narrow preferred dosage range, such as immunosuppressants, chemotherapy agents, etc.

Finally, the gelatin dosage forms of nanoparticulate active agents of the invention preferably exhibit increased bioavailability, at the same dose of the same active agent, require smaller doses, and show longer plasma half-life as compared to prior conventional active agent formulations.

C. Decreased Active Agent Dosage, Toxicity, and Dosage Volume, and Increased Active Agent Dose Loading In another aspect of the invention, the gelatin dosage forms of nanoparticulate active agents of the invention may have enhanced bioavailability such that the active agent dosage can be reduced as compared to a conventional non-nanoparticulate dosage form of the same active agent, which can result in a decrease in toxicity associated with the active agent.

In addition, greater bioavailability of the gelatin dosage forms of nanoparticulate active agents of the invention can enable a smaller active agent dosage volume. This is particularly significant for patient populations such as the elderly, juvenile, and infant.

The gelatin dosage forms of the invention can be formulated for dosages in any volume, but are preferably formulated into equivalent or smaller volumes than existing conventional dosage forms of the same active agent (i.e., non-nanoparticulate or solubilized active agent formulations). For example, the invention encompasses gelatin dosage forms formulated into a volume which is at least half that of a conventional non-nanoparticulate dosage form of the same active agent. Even smaller dosage volumes are also possible.

The maximal dose loading of the gelatin dosage forms of the invention is significantly higher than the maximal dose loading provided by conventional formulations of the same active agents. A dose loading which is double or more than that utilized in conventional, non-nanoparticulate dosage forms of the same active agent is expected to be useful.

D. The Gelatin Dosage Form Does not Require Potentially Toxic Solubilizing Agents for the Active Agent Preparation of the solid or semi-solid oral gelatin dosage form does not require solubilizing the active agent. This is significant, as prior art gelatin dosage forms required solubilization of the active agent. Such solubilization of an active agent is undesirable, as it can change the pharmacokinetic and pharmacologic characteristics of the active agent. For example, solubilization followed by precipitation of an active agent can result in a modification of the solidification state of the active agent (i.e., whether the active agent is in an amorphous or crystalline form), it can affect the stability of the active agent in the aqueous state, and it can affect how much of the active agent has returned to the solid state.

E. The Gelatin Dosage Forms of the Invention are Useful for Treating Particular Patient Populations Because of their ease of administration, compositions according to the present invention are particularly useful for the specific needs of pediatrics, geriatrics, and patients with dysphagia as well as patients with chronic dosing needs. Solid or semi-solid gelatin active agent delivery formulations are beneficial because of their ease of administration, convenience, and patient-friendly nature. It is estimated that 35% to 50% of the population finds it difficult to swallow tablets and hard gelatin capsules, particularly pediatric and geriatric patients. Solid or semi-solid gelatin active agent delivery formulations of the invention eliminate the need to swallow a tablet or capsule whole, as the dosage form "melts" upon administration.

One of the contemplated uses of the solid or semi-solid gelatin nanoparticulate active agent formulations is for pediatric patients. In formulating the gelatin pharmaceutical dosage formulation, the ability to mold the gelatin into shapes such as those that are pleasing and/or entertaining, including but not limited to, animals, letters, numbers, geometric shapes, characters, etc., is particularly useful for administration to young patients.

F. Improved Pharmacokinetic Profiles

The invention also preferably provides gelatin dosage forms of nanoparticulate active agents having a desirable pharmacokinetic profile when administered to mammalian subjects. The desirable pharmacokinetic profile of the gelatin dosage forms preferably includes, but is not limited to: (1) that the $T_{max}$ of an active agent when assayed in the plasma of a mammalian subject following administration is preferably less than the $T_{max}$ for a conventional, non-nanoparticulate form of the same active agent, administered at the same dosage; (2) that the $C_{max}$ of an active agent when assayed in the plasma of a mammalian subject following administration is preferably greater than the $C_{max}$ for a conventional, non-nanoparticulate form of the same active agent, administered at the same dosage; and/or (3) that the AUC of an active agent when assayed in the plasma of a mammalian subject following administration, is preferably greater than the AUC for a conventional, non-nanoparticulate form of the same active agent, administered at the same dosage.

The desirable pharmacokinetic profile, as used herein, is the pharmacokinetic profile measured after the initial dose of an active agent. The compositions can be formulated in any way as described herein and as known to those of skill in the art.

A preferred gelatin dosage form of the invention exhibits in comparative pharmacokinetic testing with a non-nanoparticulate formulation of the same active agent, administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, or not greater than about 10% of the $T_{max}$ exhibited by the non-nanoparticulate formulation of the same active agent.

A preferred gelatin dosage form of the invention exhibits in comparative pharmacokinetic testing with a non-nanoparticulate formulation of the same active agent, administered at the same dosage, a $C_{max}$ which is at least about 10%, at least about 20%, at least about 30%, at least about 40%, at least about 50%, at least about 60%, at least about 70%, at least about 80%, at least about 90%, or at least about 100% greater than the $C_{max}$ exhibited by the non-nanoparticulate formulation of the same active agent.

A preferred gelatin dosage composition of the invention exhibits in comparative pharmacokinetic testing with a non-nanoparticulate formulation of the same active agent, administered at the same dosage, an AUC which is at least about 10%, at least about 20%, at least about 30%, at least about 40%, at least about 50%, at least about 60%, at least about 70%, at least about 80%, at least about 90%, or at least about 100% greater than the AUC exhibited by the non-nanoparticulate formulation of the same active agent.

G. Gelatin Dosage Forms Having Combination Pharmacokinetic Profiles

In yet another embodiment of the invention, the gelatin dosage forms of the invention can comprise multiple nanoparticulate active agent compositions of either the same or different active agents. Where the active agent is the same, the compositions can differ in, for example, the active agent particle size or the active agent dosage. In addition, the gelatin dosage form can comprise one or more solubilized or conventional microparticulate particle size active agents.

For example, the gelatin dosage form can comprise a first nanoparticulate active agent composition having a nanoparticulate particle size, conferring a short $T_{max}$ and typically a higher $C_{max}$. This first nanoparticulate active agent composition can be combined with a second composition comprising: (1) the same active agent having a larger (but still nanoparticulate as defined herein) particle size, and therefore exhibiting slower absorption, a longer $T_{max}$, and typically a lower $C_{max}$; (2) the same active agent having a microparticulate particle size or which is solubilized, exhibiting a longer $T_{max}$, and typically a lower $C_{max}$; and/or (3) a different active agent having nanoparticulate particle size, microparticulate particle size, or which is solubilized.

The second, third, fourth, etc., active agent compositions can differ from the first, and from each other, for example: (1) in the effective average particle sizes of the active agent; (2) the dosage of the active agent; or (3) in the identity of the active agent. Such a combination composition can reduce the dose frequency required.

If the second active agent composition has a nanoparticulate particle size, then preferably the active agent particles of the second composition have at least one surface stabilizer associated with the surface of the active agent particles. The one or more surface stabilizers can be the same as or different from the surface stabilizer(s) present in the first active agent composition.

In another aspect of the invention, nanoparticulate active agent particles can be combined with the microparticulate particles of the same active agent to provide for a gelatin dosage form exhibiting sustained or controlled release. The combination of very small active agent particles, i.e., nanoparticulate active agent particles, in combination with larger active agent particles, i.e., micronized active agent particles, can enable obtaining the simultaneous presentation of immediate-release (IR) and controlled-release (CR) active agent components. For the purposes of this invention, "nanoparticulate" active agents have an effective average particle size of less than about 2 microns and micronized active agents have an effective average particle size of greater than about 2 microns.

The nanoparticulate active agent particles, representing the IR component, afford rapid in vivo dissolution, owing to their small size and attendant large specific surface. Alternatively, micronized active agent particles, representing the CR component, afford slower in vivo dissolution, owing to a comparatively large particle size and small attendant specific surface.

IR and CR components representing a wide range of in vivo dissolution rates (and hence, in vivo input rates for absorption) can be engineered through precise control of active agent particle size. Thus, the compositions can comprise a mixture of nanoparticulate active agent particles, wherein each population of particles has a defined size correlating with a precise release rate, and the compositions can comprise a mixture of microparticulate active agent particles, wherein each population of particles has a defined size correlating with a precise release rate.

H. The Pharmacokinetic Profiles of the Active Agent Compositions of the Invention are not Affected by the Fed or Fasted State of the Subject Ingesting the Compositions The invention encompasses a gelatin dosage form of a nanoparticulate active agent wherein the pharmacokinetic profile of the active agent is preferably not substantially affected by the fed or fasted state of a subject ingesting the composition, when administered to a human. This means that there is no substantial difference in the quantity of active agent absorbed or the rate of active agent absorption when the gelatin dosage forms are administered in the fed versus the fasted state.

The invention also encompasses a gelatin dosage form of a nanoparticulate active agent in which administration of the gelatin dosage form to a subject in a fasted state is bioequivalent to administration of the gelatin dosage form to a subject in a fed state. "Bioequivalency" is preferably established by a 90% Confidence Interval (CI) of between 0.80 and 1.25 for both $C_{max}$ and AUC under U.S. Food and Drug Administration regulatory guidelines, or a 90% CI for AUC of between 0.80 to 1.25 and a 90% CI for $C_{max}$ of between 0.70 to 1.43 under the European EMEA regulatory guidelines ($T_{max}$ is not relevant for bioequivalency determinations under USFDA and EMEA regulatory guidelines).

Benefits of a dosage form which substantially eliminates the effect of food include an increase in subject convenience, thereby increasing subject compliance, as the subject does not need to ensure that they are taking a dose either with or without food. This is significant, as with poor subject compliance an increase in the medical condition for which the active agent is being prescribed may be observed.

The difference in absorption of the gelatin dosage forms of the invention, when administered in the fed versus the fasted state, preferably is less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, or less than about 3%.

I. Bioadhesive Gelatin Dosage Forms of Nanoparticulate Active Agents

Bioadhesive gelatin dosage forms of nanoparticulate active agents according to the present invention comprise at least one cationic surface stabilizer, which are described in more detail below. Bioadhesive gelatin dosage forms of nanoparticulate active agents exhibit exceptional bioadhesion to biological surfaces, such as mucous. The term bioadhesion refers to any attractive interaction between two biological surfaces or between a biological and a synthetic surface. In the case of bioadhesive nanoparticulate active agents, the term bioadhesion is used to describe the adhesion between the nanoparticulate active agents and a biological substrate (i.e. gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

The bioadhesive gelatin dosage forms of nanoparticulate active agents of the invention are useful in any situation in which it is desirable to apply the compositions to a biological surface. The bioadhesive gelatin dosage forms coat the targeted surface in a continuous and uniform film which is invisible to the naked human eye.

A bioadhesive gelatin dosage form of a nanoparticulate active agent slows the transit of the dosage form, and some active agent particles would also most likely adhere to tissue other than the mucous cells and therefore give a prolonged exposure to the active agent, thereby increasing absorption and the bioavailability of the administered dosage.

II. Compositions

The starting nanoparticulate active agent composition, prior to formulation into a solid or semi-solid gelatin dosage form, comprises at least one active agent having an effective average particle size of less than about 2 microns and at least one surface stabilizer adsorbed on or associated with the surface of the active agent.

Surface stabilizers useful herein physically adhere on, or associate with, the surface of the nanoparticulate active agent but do not chemically react with the active agent particles or itself. Individual molecules of the surface stabilizer are preferably essentially free of intermolecular cross-linkages.

The present invention also includes gel-stabilized nanoparticulate active agent compositions together with one or more non-toxic physiologically acceptable carriers, adjuvants, or vehicles, collectively referred to as carriers. The compositions can be formulated for administration in solid or semi-solid form.

A. Active Agents

The invention can be practiced with a wide variety of active agents. The active agent is preferably poorly soluble and dispersible in at least one liquid media. Useful liquid dispersion medias include, but are not limited to, water, aqueous salt solutions, safflower oil, and solvents such as ethanol, t-butanol, hexane, and glycol. By "poorly soluble" it is meant that the active agent has a solubility in the liquid dispersion media of less than about 30 mg/ml, preferably less than about 20 mg/ml, preferably less than about 10 mg/ml, and more preferably less than about 1 mg/ml. Two or more active agents can be used in combination.

If an active agent is not poorly soluble, it can be conjugated to a salt or other substance to render the active agent poorly soluble. Thus, active agents having, for example, therapeutic, cosmetic, diagnostic, or bioengineering uses are presumed suitable for the invention.

The active agent may be present either substantially in the form of one optically pure enantiomer or as a mixture, racemic or otherwise, of enantiomers. In addition, the active agent may be in a crystalline form, semi-crystalline form, amorphous form, semi-amorphous form, or a combination thereof.

The active agent can be selected from a variety of known classes of drugs, including, for example, COX-2 inhibitors, retinoids, anticancer agents, NSAIDS, proteins, peptides, nucleotides, anti-obesity drugs, nutraceuticals, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

Examples of representative active agents useful in this invention include, but are not limited to, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, *Aloe Vera*, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

A description of these classes of active agents and a listing of species within each class can be found in Martindale, *The Extra Pharmacopoeia*, Twenty-ninth Edition (The Pharmaceutical Press, London, 1989), specifically incorporated by reference. The active agents are commercially available and/or can be prepared by techniques known in the art.

B. Surface Stabilizers

The choice of a surface stabilizer is non-trivial and usually requires extensive experimentation to realize a desirable formulation.

Exemplary useful surface stabilizers include, but are not limited to, known organic and inorganic pharmaceutical excipients. Such excipients include various polymers, low molecular weight oligomers, natural products, and surfactants. Exemplary surface stabilizers include nonionic, anionic, cationic, ionic, and zwitterionic surfactants. Combinations of more than one surface stabilizer can be used in the invention.

Representative examples of surface stabilizers include hydroxypropyl methylcellulose, hydroxypropylcellulose, polyvinylpyrrolidone, random copolymers of vinyl pyrrolidone and vinyl acetate, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550200 and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2C(O)N(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl, β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quaternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUA™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quaternary phosphorous compound, a pyridinium compound, an anilinium compound, an ammonium compound, a hydroxylammonium compound, a primary ammonium compound, a secondary ammonium compound, a tertiary ammonium compound, and quaternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where $n>1$;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of*

*Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

C. Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

By "an effective average particle size of less than about 2000 nm" it is meant that at least about 50% of the active agent particles have a particle size less than about 2000 nm when measured by the above techniques. In other embodiments of the invention, at least about 70%, at least about 90%, at least about 95%, or at least about 99% of the active agent particles have a particle size less than the effective average, i.e., less than about 2000 nm.

In other embodiments of the invention, the effective average particle size of the active agent particles is less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm.

In the present invention, the value for D50 of a nanoparticulate active agent composition is the particle size below which 50% of the active agent particles fall, by weight. Similarly, D90 is the particle size below which 90% of the active agent particles fall, by weight.

For conventional or microparticulate active agents, by "an effective average particle size of greater than about 2 microns" it is meant that at least 50% of the active agent particles have a particle size greater than about 2 microns, when measured by the above techniques.

D. The Gel Forming Substance

The gel forming substance can be a natural, semi-synthetic, or synthetic gelatin, or a chemical or physical gel. At least one natural or synthetic gel forming substance is used in the inventive formulations.

Natural gel forming substances include but are not limited to algal (e.g., agar, furcelleran, alginate, and carrageenan), botanical (e.g., plant extracts, gum arabic, tragacanth, karaya, ghatti seed gums, guar gum, and locust bean gum), microbial (e.g., xanthan, pullulan, scleroglucan, curdlan, dextran, and gellan), animal (e.g., chitin and chitosan, chrondroitin sulfate, dermatan sulfate, heparin, keratan sulfate, and hyaluronic acid), and others as described in Park et al., "Biodegradable Hydrogels for Drug Delivery" (Technomic Publishing Company, Inc., 1993).

Synthetic gel forming substances include but are not limited to water-soluble polymers containing complexing groups, which can be crosslinked to form gels. Examples of water-soluble monomers include but are not limited to acrylic acid, methacrylic acid, acrylamide, N-alkylacrylamide, methacrylamide, vinylpyrrolidone, methyl methacrylate, hydroxyethyl methacrylate, and vinyl pyridine which can be crosslinked with, e.g., low molecular weight crosslinking agents, such as N,N'-methylenebisacrylamide and macromolecules, such as proteins. Basically, any molecule with at least two C=C bonds should be able to function as a crosslinking agent in the copolymerization with vinyl monomers and others, as described in "Biodegradable Hydrogels for Drug Delivery".

E. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Because many drugs have an unpleasant taste, the use of taste masking excipients may be added to the gelatin composition to achieve a composition which is pleasant tasting and easily administered. In addition to pleasant tasting flavors, interesting coloring agents can be added to the formulation.

Such taste masking can be accomplished, for example, by the addition of one or more sweet tasting excipients, by coating the nanoparticulate active agent and one or more surface stabilizers with a sweet tasting excipient, and/or by coating a dosage form of the nanoparticulate active agent, one or more surface stabilizers, and excipients with a sweet tasting excipient.

Examples of filling agents are lactose monohydrate, lactose anhydrous, and various starches; examples of binding agents are various celluloses and cross-linked polyvinylpyrrolidone, microcrystalline cellulose, such as Avicel® PH 101 and Avicel® PH 102, microcrystalline cellulose, and silicified microcrystalline cellulose (SMCC).

Suitable lubricants, including agents that act on the flowability of the powder to be compressed, are colloidal silicon dioxide, such as Aerosil® 200; talc, stearic acid, magnesium stearate, calcium stearate, and silica gel.

Examples of sweeteners are any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicele® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

F. Quantities of Nanoparticulate Active Agent Composition and Gel forming Substance The relative amount of nanoparticulate active agent composition in the gelatin dosage forms of the invention can vary widely and can depend upon, for example, the active agent and surface stabilizer(s) selected for delivery, the melting point of the active agent and surface stabilizer, the water solubility of the active agent and surface stabilizer, the surface tension of water solutions of the active agent and surface stabilizer, etc. The active agent may be present in any amount which is sufficient to elicit a therapeutic effect.

The concentration of the at least one active agent can vary from about 99.5% to about 0.001%, from about 95% to about 0.1%, or from about 90% to about 0.5%, by weight, based on the total combined weight of the active agent and surface stabilizer, not including other excipients.

The concentration of the at least one surface stabilizer can vary from about 0.5% to about 99.999%, from about 5.0% to about 99.9%, and from about 10.0% to about 99.5%, by weight, based on the total combined dry weight of the active agent and surface stabilizer, not including other excipients.

The at least one gel forming substance can be present in an amount of about 0.5% to about 60%, about 3% to about 40%, or about 5% to about 20%, by weight, based on the total weight of the active agent, surface stabilizer, and gel forming substance.

III. Methods of Making Solid or Semi-Solid Gelatin Nanoparticulate Active Agent Compositions In another aspect of the invention there is provided a method of preparing solid or semi-solid gelatin dosage forms of nanoparticulate active agents. The method comprises combining: (1) a nanoparticulate active agent composition of at least one active agent and at least one surface stabilizer, wherein the active agent has an effective average particle size of less than about 2000 nm, and (2) at least one gel forming substance, which exhibits gelation sufficient to retain excess water in a solid or semi-solid form, to form a solid dose matrix surrounding the nanoparticulate active agent composition. The method does not comprise solubilizing the active agent. This composition is used to form a solid dose formulation, wherein the gelatin solid dose composition achieves redispersion upon administration to a patient.

Nanoparticulate active agent compositions can be made using, for example, milling, precipitation, or homogenization techniques. Exemplary methods of making nanoparticulate active agent compositions are described in U.S. Pat. No. 5,145,684. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

In a typical manufacturing process, the solid or semi-solid gelatin nanoparticulate matrix composition is prepared by mixing gelatin at an appropriate concentration and warming the mixture in a water bath, such as at about 50° C. A warmed amount of a nanoparticulate active agent dispersion (comprising at least one active agent and at least one surface stabilizer) is slowly added to the molten gelatin with an overhead mixer and mixed, such as for about 10 minutes. The nanoparticulate active agent dispersion can also be heated in a water bath of about 50° C. Upon completion of mixing, the molten mixture is homogenized. When the homogenization is completed, the formulation is dispensed into a mold and refrigerated until formed.

The gelatin formulations of the invention can be formulated into solid or semi-liquid dosage formulations, such as controlled release formulations, solid dose fast melt formulations, lyophilized formulations, aerosol formulations, tablets, capsules, lozenges, etc.

1. Milling to Obtain Nanoparticulate Active Agent Dispersions

Milling an active agent to obtain a nanoparticulate dispersion for subsequent formulation into a solid or serni-solid gel dosage form comprises dispersing particles of at least one active agent in a liquid dispersion media in which the active agent is poorly soluble, followed by applying mechanical means in the presence of grinding media to reduce the particle size of the active agent to the desired effective average particle size. The dispersion media can be, for example, water, safflower oil, ethanol, t-butanol, glycerin, polyethylene glycol (PEG), hexane, or glycol.

The active agent particles can be reduced in size in the presence of at least one surface stabilizer. Alternatively, the active agent particles can be contacted with one or more surface stabilizers after attrition. Other compounds, such as a diluent, can be added to the active agent/surface stabilizer composition during the size reduction process. Dispersions can be manufactured continuously or in a batch mode.

2. Homogenization to Obtain Nanoparticulate Active Agent Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing active agent particles in a liquid dispersion media, followed by subjecting the dispersion to homogenization to reduce the particle size of the active agent to the desired effective average particle size. The active agent particles can be reduced in size in the presence of at least one surface stabilizer. Alternatively, the active agent particles can be contacted with one or more surface stabilizers either before or after particle size reduction. Other compounds, such as a diluent, can be added to the active agent/surface stabilizer composition either before, during, or after the size reduction process. Dispersions can be manufactured continuously or in a batch mode.

C. Administration of Solid or Semi-Solid Gelatin Dosage Form of a Nanoparticulate Active Agent The present invention provides a method of treating a subject, including humans and animals, requiring the rapid availability and ease of administration of an active agent, and in particular a poorly water soluble active agent. The method comprises administering to the subject an effective amount of a solid or semi-solid gelatin dosage form of a nanoparticulate active agent. The gelatin dosage form melts, and the component nanoparticulate active agent particles redisperse, upon administration.

The composition can be formulated into any suitable dosage form, such as a immediate release formulation, controlled release formulation, fast melt formulation, delayed release formulation, extended release formulation, pulsatile release formulation, and mixed immediate release and controlled release formulation.

An alternative method of administration involves administering an effective amount of a solid or semi-solid gelatin dosage form of a nanoparticulate active agent which redisperses upon administration to a fasted patient. A fasted patient is defined as a patient that has not ingested food for a period of time prior to administration of the gelatin dosage form. As shown in the examples below, it was surprisingly discovered that the gelatin dosage forms of the invention have an enhanced efficacy in a fasted patient in comparison to administration of a nanoparticulate active agent dispersion.

In general, the compositions of the invention are administered via any pharmaceutically acceptable method to a subject in need thereof using a level of active agent that is sufficient to provide the desired physiological effect, such as oral, rectal, vaginal, local, buccal, and topical administration. The subject may be a domestic animal or pet but preferably is a human subject. The level of active agent needed to give the desired physiological result is readily determined by one of ordinary skill in the art by referring to standard texts, such as *Goodman and Gillman* and the *Physician's Desk Reference*.

The following examples are given to illustrate the present invention. It should be understood, however, that the invention is not to be limited to the specific conditions or details described in these examples. Throughout the specification, any and all references to publicly available documents are specifically incorporated into this patent application by reference.

EXAMPLE 1

The purpose of this example was to prepare a nanoparticulate gelatin formulation of Compound A, having analgesic properties.

A nanoparticulate dispersion of Compound A was prepared, comprising 20% Compound A, 4% Plasdone® S630 (a copolymer of vinyl pyrrolidone and vinyl acetate from ISP), and 0.8% dioctylsulfosuccinate (DOSS). The dispersion was prepared by milling Compound A, Plasdone® S630, and DOSS with a Dyno®-Mill (Type: KDL; Mfg.: Willy A Bachofen AG, Basel, Switzerland) equipped with a 300 cc recirculation chamber using a 500 µm milling media of type Polymill 500® for 6 hrs at 10° C.

The initial particle size was measured using a Horiba LA-910 Static Light Scattering Particle Analyzer (Horiba Instruments, Irvine, Calif.). The mean particle size of Compound A dispersion was 138 nm with a D90 of 202 nm.

The solid gelatin matrix of nanoparticulate Compound A was prepared by warming a 20% gelatin: 80% water mixture (250 Bloom Type B NF Bone Gelatin manufactured by Kind & Knox, Sioux City, Iowa.) at 50° C. in a water bath.

Next, the nanoparticulate dispersion of 20% Compound A, 4% Plasdone® S630, and 0.8% dioctylsulfosuccinate (DOSS) was heated in a 50° C. water bath until the dispersion reached 50° C. The dispersion was slowly added to the molten gelatin in a 1:1 ratio (nanoparticulate Compound A dispersion:gelatin solution) with an overhead mixer and mixed for 10 minutes. The resultant gelatin/nanoparticulate Compound A dispersion had the following composition: 10% Compound A, 2% Plasdone® S630, 0.4% dioctylsulfosuccinate (DOSS), and 10% gelatin with the remaining 77.6% of the composition being water.

Upon completion of mixing, a pump was connected and the molten mixture was homogenized at 12000 rpm for approximately 3 minutes. When the homogenization was completed, the formulation was dispensed into a mold and refrigerated until formed.

EXAMPLE 2

The purpose of this example was to prepare a nanoparticulate Ketoprofen gelatin formulation. Ketoprofen is a well-known nonsteroidal anti-inflammatory agent (NSAID).

A nanoparticulate Ketoprofen dispersion was prepared, comprising 30% ketoprofen and 3% polyvinylpyrrolidone (PVP k90). The dispersion was prepared by milling ketoprofen and PVP with a Dyno®-Mill (Type: KDL; Mfg.: Willy A Bachofen AG, Basel, Switzerland) equipped with a 150 cc batch chamber using a 500 µm milling media of type Polymill 500® for 2 hrs at 10° C.

The initial particle size was measured using a Horiba LA-910 Static Light Scattering Particle Analyzer (Horiba Instruments, Irvine, Calif.). The mean particle size of the ketoprofen dispersion was 183 nm, with a D50 and D90 of 178 nm and 249 nm, respectively.

The solid gelatin matrix of nanoparticulate ketoprofen was prepared by warming a 20% gelatin: 80% water mixture (250 Bloom Type B NF Bone Gelatin manufactured by Kind & Knox, Sioux City, Iowa.) at 50° C. in a water bath.

A nanoparticulate dispersion of 30% ketoprofen and 3% PVP heated in a 50° C. water bath until the dispersion reached 50° C. The dispersion was slowly added to the molten gelatin in a 1:1 ratio (nanoparticulate ketoprofen dispersion:gelatin solution) with an overhead mixer and mixed for 10 minutes. The resultant gelatin/nanoparticulate ketoprofen dispersion had the following composition; 15% ketoprofen, 1.5% PVP, and 10% gelatin with the remaining 73.5% of the composition being water.

Upon completion of mixing, a pump was connected and the molten mixture was homogenized at 12000 rpm for approximately 3 minutes. When the homogenization was completed, the formulation was dispensed into a mold and refrigerated until formed.

EXAMPLE 3

The purpose of this example was to compare the redispersion properties of various solid or semi-solid nanoparticulate naproxen gelatin dosage formulations. Naproxen is a well-known anti-inflammatory, analgesic, and antipyretic agent.

A first nanoparticulate dispersion of naproxen was prepared, comprising 20% naproxen and 2% PVP k90. The dispersion was prepared by milling naproxen and PVP with a Dyno®-Mill (Type: KDL; Mfg.: Willy A Bachofen AG, Basel, Switzerland) equipped with a 300 cc batch chamber using a 500 µm milling media of type Polymill 500® for 5 hrs at 10° C.

The initial particle size was measured using a Horiba LA-910 Static Light Scattering Particle Analyzer (Horiba Instruments, Irvine, Calif.). The mean particle size of the first naproxen dispersion was 154 nm, with a D50% and a D90% of 145 and 222 nm, respectively.

A second nanoparticulate naproxen dispersion was prepared, comprising 40% naproxen and 4% PVP k90. The dispersion was prepared by milling naproxen and PVP in a similar manner to the first dispersion.

The initial particle size was measured using a Horiba LA-910 Static Light Scattering Particle Analyzer (Horiba Instruments, Irvine, Calif.). The mean particle size of the second naproxen dispersion was 158 nm, with a D50% and a D90% of 152 and 216 nm, respectively.

Two gelatin formulations of nanoparticulate naproxen were prepared utilizing the two nanoparticulate naproxen compositions.

The first solid gelatin matrix of nanoparticulate naproxen was prepared by warming a 10% gelatin: 90% water mixture (250 Bloom Type B NF Bone Gelatin manufactured by Kind & Knox, Sioux City, Iowa.) at 50° C. in a water bath. Next, the nanoparticulate dispersion of 20% naproxen and 2% PVP was heated in a 50° C. water bath until the dispersion reached 50° C. The dispersion was slowly added to the molten gelatin in a 0.25:1 ratio (nanoparticulate naproxen dispersion: gelatin solution) with an overhead mixer and mixed for 10 minutes. The resultant gelatin/nanoparticulate naproxen dispersion had the following composition: 4% naproxen, 0.4% PVP, and 8% gelatin with the remaining 87.6% of the composition being water.

The second solid gelatin matrix of nanoparticulate naproxen was prepared by warming a 30% gelatin: 70% water mixture (250 Bloom Type B NF Bone Gelatin manufactured by Kind & Knox, Sioux City, Iowa.) at 50° C. in a water bath. Next, the nanoparticulate naproxen dispersion of 40% naproxen and 4% PVP was heated in a 50° C. water bath until the dispersion reached 50° C. The dispersion was slowly added to the molten gelatin in a 1:0.5 ratio (nanoparticulate naproxen dispersion:gelatin solution) with an overhead mixer and mixed for 10 minutes. The resultant gelatin/nanoparticulate naproxen dispersion had the following composition; 26.7% naproxen, 2.7% PVP, and 10% gelatin with the remaining 60.6% of the composition being water.

Upon completion of mixing, a pump was connected and the molten mixture was homogenized at 12000 rpm for approximately 3 minutes. When the homogenization was completed, each formulation was dispensed into a mold and refrigerated until formed.

The two gelatin formulations were redispersed in water at 35-40° C. Naproxen particle size following redispersion was measured using a Horiba LA910 particle sizer. The results of the redispersion tests are shown in Table 1, below.

TABLE 1

Redispersion Nanoparticulate Naproxen Gelatin Formulations

| Composition | | Redispersed Particle Size (nm) | | |
| --- | --- | --- | --- | --- |
| Redispersion Media | Formulation | Mean | D90 | % under 1000 nm |
| Water | 4% Naproxen: 8% Gelatin (original mean particle size of 154 nm) | 257 | 383 | 100% |
| Water | 26.7% Naproxen: 10% Gelatin (original mean particle size of 158 nm) | 202 | 276 | 100% |

The results dramatically show the successful redispersion of the nanoparticulate naproxen gelatin formulations.

EXAMPLE 4

The purpose of this example was to investigate the redispersibility properties of the semi-solid gelatin nanoparticulate Compound A dosage formulation manufactured according to Example 1.

The composition of the dosage form was 10% Compound A, 2% Plasdone® S630, 0.4% dioctylsulfosuccinate (DOSS), and 10% gelatin with the remaining 77.6% of the composition being water.

The gelatin formulation was redispersed in Simulated Gastric Fluid (SGF) at 35-40° C. Compound A particle size was measured using a Horiba LA910 particle sizer. The results of the redispersion tests are shown in Table 2, below.

TABLE 2

Redispersion of Nanoparticulate Compound A Gelatin Formulations

| Composition | | Redispersed Particle Size (nm) | | |
| --- | --- | --- | --- | --- |
| Media | Final Formulation | Mean | D90 | % under 1000 nm |
| SGF | 10% Compound A: 10% Gelatin (original particle size of 138 nm) | 312 | 187 | 98.6% |

The results dramatically show the successful redispersion of the nanoparticulate Compound A gelatin formulations.

EXAMPLE 5

The purpose of this example was to investigate the redispersibility properties of the semi-solid gelatin nanoparticulate ketoprofen dosage formulation manufactured according to Example 2.

The composition of the dosage form was 15% ketoprofen, 1.5% PVP, and 10% gelatin with the remaining 73.5% of the composition being water.

The gelatin formulation was redispersed in water at 35-40° C. Ketoprofen particle size was measured using a Horiba LA910 particle sizer. The results of the redispersion tests in water and simulated gastric fluid (SGF), are shown in Table 3, below.

TABLE 3

Redispersion of Nanoparticulate Ketoprofen Gelatin Formulations

| Composition | | Redispersed Particle Size (nm) | | |
| --- | --- | --- | --- | --- |
| Media | Final Formulation | Mean | D90* | % under 1000 nm |
| Water | 15% Ketoprofen: 10% Gelatin (original mean particle size of 183 nm) | 1058 | 390 | 92.3% |
| SGF | 15% Ketoprofen: 10% Gelatin (original mean particle size of 183 nm) | 245 | 333 | 100.0% |

The results dramatically show the successful redispersion of the nanoparticulate ketoprofen gelatin formulations.

EXAMPLE 6

The purpose of this example was to evaluate the in vivo performance of nanoparticulate ketoprofen gelatin formulations administered orally to fasted beagles.

Four ketoprofen formulations were used in the study: (1) commercial ketoprofen (generic ketoprofen 50 mg capsules manufactured by Lederle), having an approximate particle size of 500 microns; (2) a nanoparticulate ketoprofen dispersion, preparation of which is described below; (3) a 5% soft oral gelatin formulation, preparation of which is described below; and (4) a 20% hard oral gelatin formulation, preparation of which is described below.

A nanoparticulate dispersion of ketoprofen was prepared, comprising 30% ketoprofen, 3% PVP k29/32, and 0.15% sodium lauryl sulphate (SLS). The dispersion was prepared by milling ketoprofen, PVP and SLS with a NanoMill®-2 (Mfg.: Netzch, Exton, P.A., U.S.A.) using a 500 µm milling media of type Polymill 500® at 10° C. until the desired particle size was achieved.

The initial particle size was measured using a Horiba LA-910 Static Light Scattering Particle Analyzer (Horiba Instruments, Irvine, Calif.). The mean particle size of the Ketoprofen dispersion was 153 nm, with a D50% and a D90% of 148 and 208 nm, respectively.

Two gelatin formulations of nanoparticulate ketoprofen were prepared utilizing the nanoparticulate ketoprofen composition.

The first solid gelatin matrix of nanoparticulate ketoprofen—termed "5% soft oral gelatin formulation," was prepared by warming a 10% gelatin: 90% water mixture (250 Bloom Type B NF Bone Gelatin manufactured by Kind & Knox, Sioux City, Iowa.) at 50° C. in a water bath. Next, the nanoparticulate ketoprofen dispersion of comprising 30% ketoprofen, 3% PVP k29/32, and 0.15% SLS was heated in a 50° C. water bath until the dispersion reached 50° C. The warmed ketoprofen dispersion was then slowly added to the molten gelatin in a 1:1 ratio (nanoparticulate ketoprofen dispersion:gelatin solution) with an overhead mixer and mixed for 10 minutes. The resultant gelatin/nanoparticulate ketoprofen dispersion had the following composition: 10% ketoprofen, 1% PVP, 0.5% SLS and 5% gelatin with the remaining 83.5% of the composition being water.

The second solid gelatin matrix of nanoparticulate ketoprofen—termed "20% hard oral gelatin formulation," was prepared by warming a 40% gelatin: 60% water mixture (250 Bloom Type B NF Bone Gelatin manufactured by Kind & Knox, Sioux City, Iowa.) at 50° C. in a water bath. Next, the nanoparticulate ketoprofen dispersion of comprising 30% ketoprofen, 3% PVP k29/32, and 0.15% SLS was heated in a 50° C. water bath until the dispersion reached 50° C. The warmed ketoprofen dispersion was then slowly added to the molten gelatin in a 1:1 ratio (nanoparticulate ketoprofen dispersion:gelatin solution) with an overhead mixer and mixed for 10 minutes. The resultant gelatin/nanoparticulate ketoprofen dispersion had the following composition: 10% ketoprofen, 1% PVP, 0.5% SLS and 20% gelatin with the remaining 68.5% of the composition being water.

Upon completion of mixing, a pump was connected and the molten mixture was homogenized at 12000 rpm for approximately 3 minutes. When the homogenization was completed, each formulation was dispensed into a mold and refrigerated until formed.

Twenty dogs were used in the study.
(a) 8 dogs were administered commercial ketoprofen (generic ketoprofen 50 mg capsules manufactured by Lederle), having an approximate particle size of 500 microns.
(b) 4 dogs were administered a 50 mg dose of a nanoparticulate crystalline dispersion of ketoprofen (NCD);
(c) 4 dogs were administered a 50 mg dose of ketoprofen in a 5% soft oral gelatin formulation; and
(d) 4 dogs were administered a 50 mg dose of ketoprofen in a 20% hard oral gelatin formulation.

Administration was by oral gavage to the back of the throat, whereby the dogs swallowed the formulations. As determined from FIG. 1, the gelatin formulations had a faster onset of action, as the mean peak plasma level concentration ($C_{max}$) of the 5% gelatin formulation was 17.5 µg/ml at twenty minutes after administration, which corresponds to an onset of action rate as determined from blood plasma levels of 0.85 µg/min. The hard gelatin (20% gelatin) also provided rapid onset of action and exhibited a $C_{max}$ of 19.9 µg/ml, which corresponds to an onset of action rate as determined from blood plasma levels of 1 µg/min.

By comparison, the commercial dosage exhibited a $C_{max}$ of 10.6 µg/ml, corresponding to an onset of action rate as determined from blood plasma levels of 0.5 µg/min. The NCD performed similarly, exhibiting a $C_{max}$ of 11.145 µg/ml, corresponding to an onset of action rate as determined from blood plasma levels of 0.52 µg/min.

Figure 2:
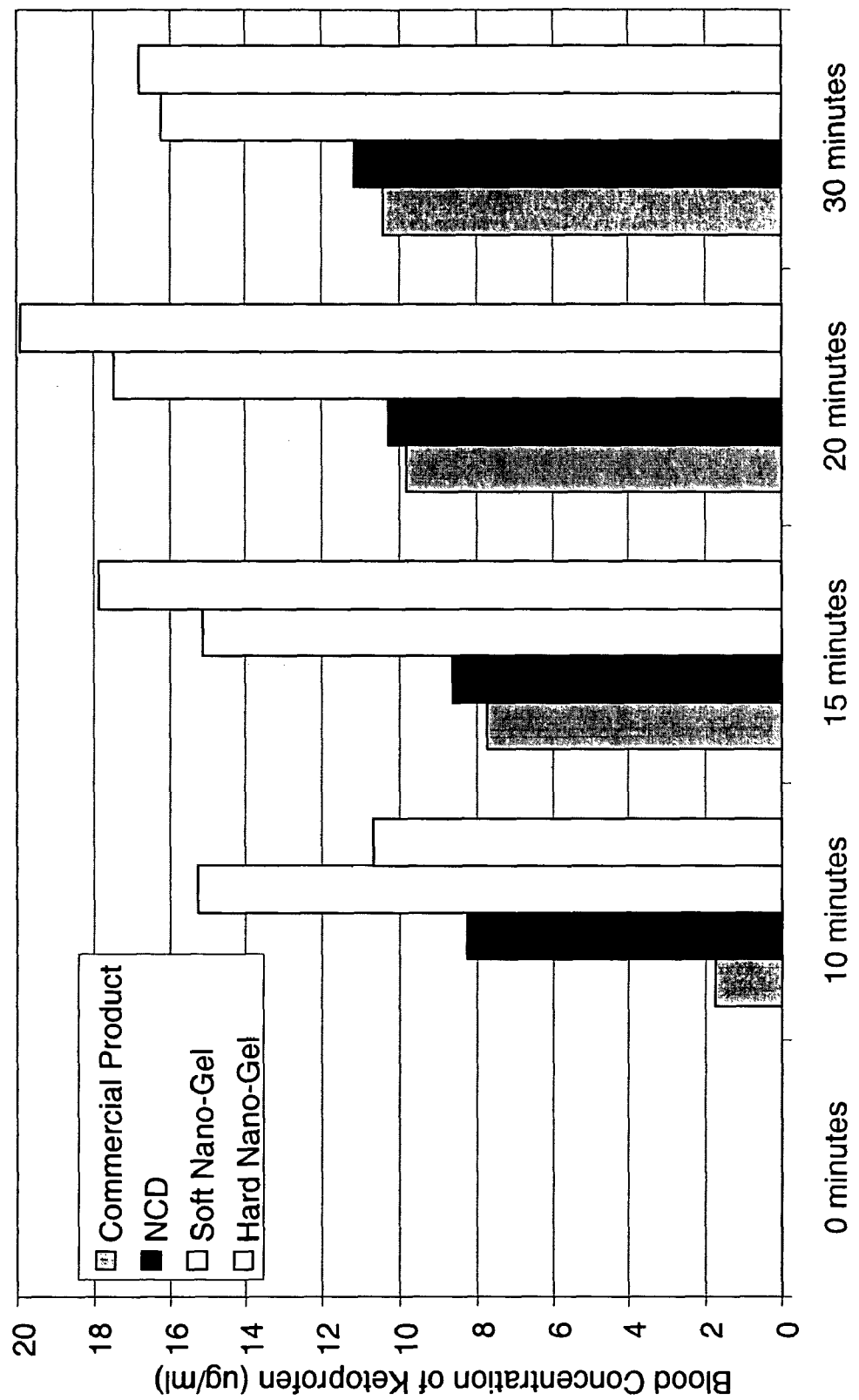
FIG. 2: Shows the blood levels of ketoprofen at 10 min., 15 min., 20 min., and 30 min. following oral administration of four different 50 mg ketoprofen dosage formulations: (a) a 20% nanoparticulate gelatin ketoprofen formulation; (b) a 5% nanoparticulate gelatin ketoprofen formulation; (c) a nanoparticulate ketoprofen liquid dispersion formulation; and (d) a commercial dose of conventional ketoprofen (generic ketoprofen 50 mg capsules manufactured by Lederle). The surface stabilizers in formulations (a)-(c) are PVP k29/32 and SLS.

FIG. 2 clearly shows that the soft nanoparticulate gel dosage form (5% gelatin) initially exhibits the highest blood concentration of ketoprofen, whereas the hard nanoparticulate gel dosage form (20% gelatin), while exhibiting a slower onset that the soft nanogel, ultimately delivers more ketoprofen from the gelatin.

EXAMPLE 7

The purpose of this example was to evaluate the in vivo performance of nanoparticulate ketoprofen gelatin formulations administered bucally to fasted beagles. The ketoprofen formulations used in this study were the same as in example 6.

Twenty dogs were used in the study.
(a) 8 dogs were administered commercial ketoprofen (generic ketoprofen 50 mg capsules manufactured by Lederle);
(b) 4 dogs were administered a 50 mg dose of a nanoparticulate crystalline dispersion of ketoprofen (NCD);
(c) 4 dogs were administered a 50 mg dose of ketoprofen in a 5% soft oral gelatin formulation; and
(d) 4 dogs were administered a 50 mg dose of ketoprofen in a 20% hard oral gelatin formulation.

Administration was accomplished by placing the dosage under the tongues of the individual dogs and muzzling the dogs to allow for absorption with checking for complete dissolution of the dosage form after 1 minute.

Figure 3:
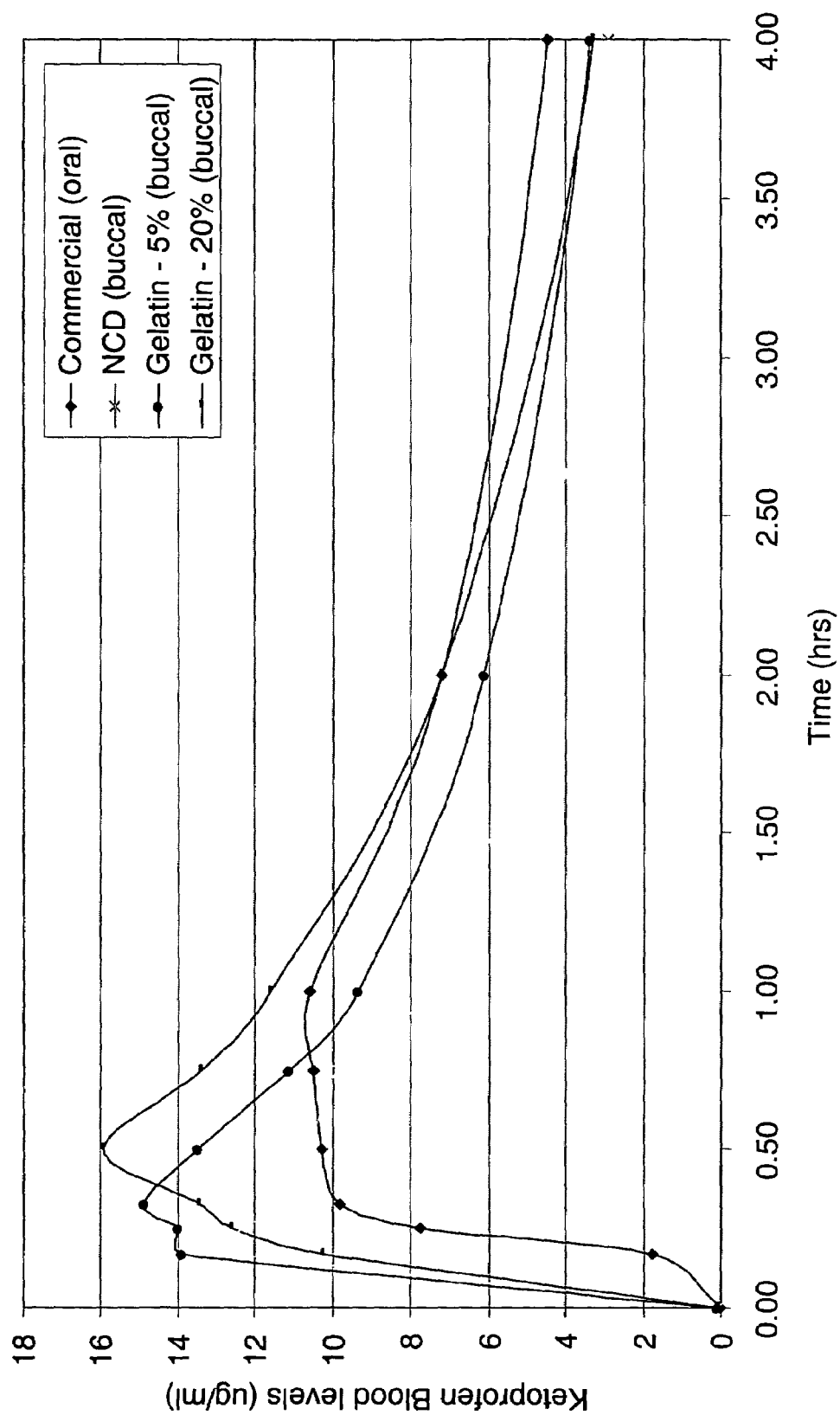
FIG. 3: Shows the blood levels of ketoprofen over a 4 hour time period following buccal administration of four different 50 mg ketoprofen dosage formulations: (a) a 5% nanoparticulate gelatin ketoprofen formulation; (b) a 20% nanoparticulate gelatin ketoprofen formulation; (c) a nanoparticulate ketoprofen liquid dispersion formulation; and (d) a commercial dose of conventional ketoprofen (generic ketoprofen 50 mg capsules manufactured by Lederle). The surface stabilizers in formulations (a)-(c) are PVP k29/32 and SLS.

As determined from FIG. 3, the gelatin formulations had a faster onset of action, as the mean peak plasma level concentration ($C_{max}$) of the soft gelatin dosage form (5% gelatin) was 14.89 µg/ml at twenty minutes after administration, which corresponds to an onset of action rate as determined from blood plasma levels of 0.75 µg/min. The hard gelatin dosage form (20% gelatin) also provided rapid onset of action and exhibited a $C_{max}$ of 15.95 µg/ml, which corresponds to an onset of action rate as determined from blood plasma levels of 0.67 µg/min.

By comparison, the commercial dosage exhibited a $C_{max}$ of 10.6 µg/ml, corresponding to an onset of action rate as determined from blood plasma levels of 0.5 µg/min. The ketoprofen NCD performed similarly, exhibiting a $C_{max}$ of 12.37 µg/ml, corresponding to an onset of action rate as determined from blood plasma levels of 0.56 µg/min.

Figure 4:
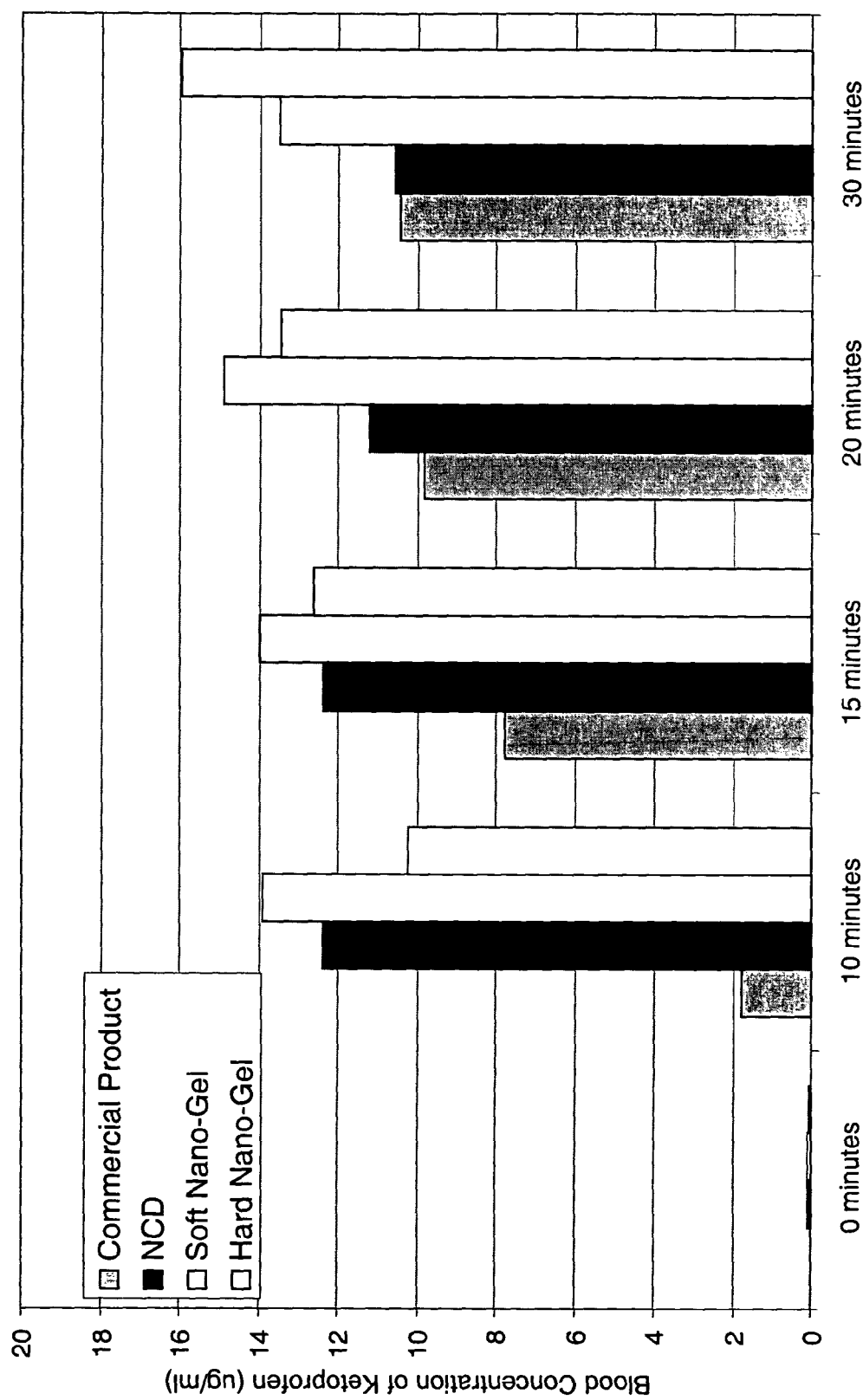
FIG. 4: Shows the blood levels of ketoprofen at 10 min., 15 min., 20 min., and 30 min. following buccal administration of four different 50 mg ketoprofen dosage formulations: (a) a 5% nanoparticulate ketoprofen gelatin formulation; (b) a 20% nanoparticulate ketoprofen gelatin formulation; (c) a nanoparticulate ketoprofen liquid dispersion formulation; and (d) a commercial dose of conventional ketoprofen (generic ketoprofen 50 mg capsules manufactured by Lederle). The surface stabilizers in formulations (a)-(c) are PVP k29/32 and SLS.
Figure 5:
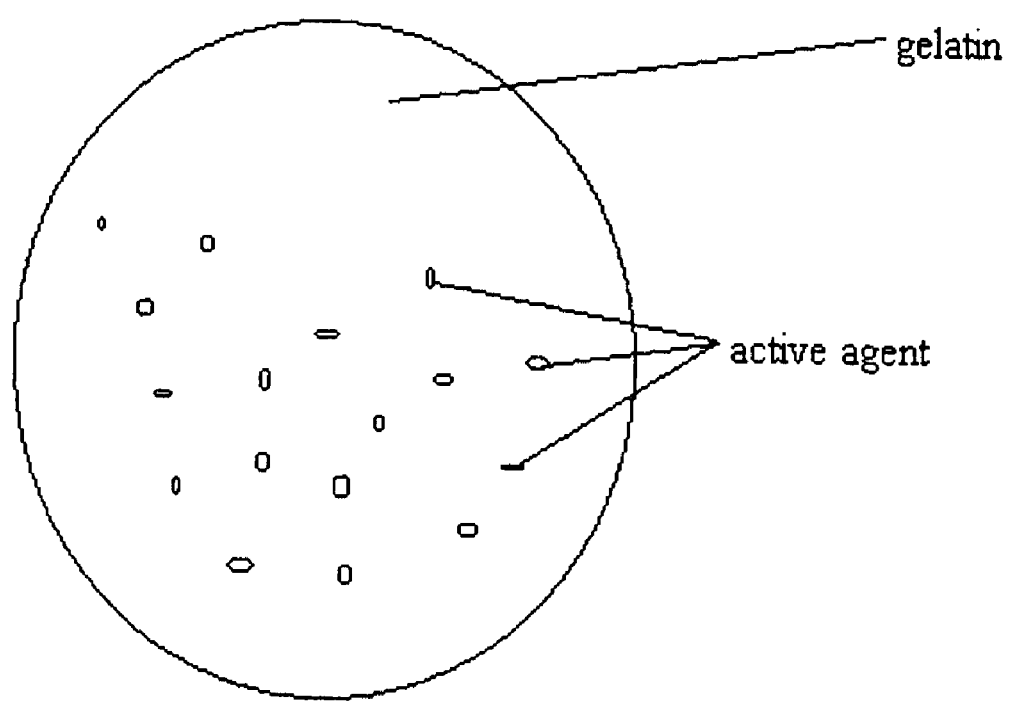
FIG. 5: Nanoparticulate active agent dispersed in gelatin, which functions to stabilize the nanoparticles of the active agent.

FIG. 4 clearly shows that the soft nanoparticulate gel dosage form (5% gelatin) initially exhibits the highest blood concentration of ketoprofen, whereas the hard nanoparticulate gel dosage form (20% nanogel), while exhibiting a slower onset that the soft nanogel, ultimately delivers more ketoprofen from the gelatin.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A homogenous solid or semi-solid gelatin pharmaceutical composition comprising:
   (a) particles of at least one active agent having an effective average particle size of less than about 2000 nm prior to inclusion in the solid or semi-solid gelatin pharmaceutical composition;
   (b) at least one surface stabilizer adsorbed on the surface of the particles;
   (c) water in the amount from about 45% to about 90% based on the total weight of the composition; and
   (d) a gel matrix of at least one gel forming substance, selected from the group consisting of a natural gelatin, a semi-synthetic gelatin, and a synthetic gelatin, the gel forming substance in an amount which exhibits gelation sufficient to retain the water,
   wherein the nanoparticulate active agent particles with the adsorbed surface stabilizer are homogenously dispersed throughout the gel matrix.

2. The composition of claim 1, wherein the concentration of the at least one active agent is selected from the group consisting of from about 99.5% to about 0.001%, from about 95% to about 0.1%, and from about 90% to about 0.5%, by weight, based on the total combined weight of the at least one active agent and at least one surface stabilizer, not including other excipients.

3. The composition of claim 1, wherein the concentration of the at least one surface stabilizer is selected from the group consisting of from about 0.5% to about 99.999%, from about 5.0% to about 99.9%, and from about 10% to about 99.5%%, by weight, based on the total combined dry weight of the at least one active agent and at least one surface stabilizer, not including other excipients.

4. The composition of claim 1, wherein the concentration of the at least one gel forming substance is selected from the group consisting of from about 0.5% to about 60%, from about 3% to about 40%, and from about 5% to about 20%, by weight, based on the total weight of the composition.

5. The composition of claim 1, wherein the gel forming substance is a natural gelatin selected from the group consisting of algal, botanical, microbial, and animal.

6. The composition of claim 5, wherein the gel forming substance is a natural gelatin selected from the group consisting of agar, furcelleran, alginate, carrageenan, plant extracts, gum arabic, tragacanth, karaya, ghatti seed gums, guar gum, locust bean gum, xanthan, pullulan, scleroglucan, curdlan, dextran, gellan, chitin, chitosan, chrondroitin sulfate, dermatan sulfate, heparain, keratan sulfate, and hyaluronic acid.

7. The composition of claim 1, wherein the gel forming substance is a synthetic gelatin which is a water-soluble polymer containing complexing groups which is crosslinked to form a gel.

8. The composition of claim 7, wherein the water-soluble polymer is selected from the group consisting of acrylic acid, methacrylic acid, acrylamide, N- alkylacrylamide, methacrylamide, vinylpyrrolidone, methyl methacrylate, hydroxyethyl methacrylate, and vinyl pyridine.

9. The composition of claim 7, wherein the complexing group is selected from the group consisting of N,N'-methylenebisacrylamide and proteins.

10. The composition of claim 1, wherein the effective average particle size of the active agent particles is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm.

11. The composition of claim 1, wherein the composition has been molded into a shape selected from the group consisting of a geometric shape, an animal shape, a numeric shape, a character shape, and an alphabet shape.

12. The composition of claim 1, wherein the composition is formulated for administration via a route selected from the group consisting of oral, rectal, vaginal, local, buccal, and topical.

13. The composition of claim 1 formulated into a dosage form selected from the group consisting of immediate release formulation, controlled release formulation, fast melt formulation, delayed release formulation, extended release formulation, pulsatile release formulation, and mixed immediate release and controlled release formulation.

14. The composition of claim 1, wherein the composition further comprises one or more pharmaceutically acceptable excipients, carriers, or a combination thereof.

15. The composition of claim 1, wherein the at least one active agent is in the form selected from the group consisting of crystalline particles, amorphous particles, or semi-crystalline particles.

16. The composition of claim 1, wherein the at least one active agent is poorly soluble in at least one liquid media, wherein "poorly soluble" is defined as a solubility in the liquid media selected from the group consisting of less than about 30 mg/mL, less than about 20 mg/mL, less than about 10 mg/mL, and less than about 1 mg/mL.

17. The composition of claim 16, wherein the liquid media is selected from the group consisting of water, safflower oil, ethanol, t-butanol, glycerin, polyethylene glycol (PEG), hexane, and glycol.

18. The composition of claim 1, wherein the at least one active agent has been rendered poorly soluble in at least one liquid media by conjugation to a salt or other suitable substance.

19. The composition of claim 1, wherein the at least one active agent is selected from the group consisting of COX-2 inhibitors, anticancer agents, NSAIDS, proteins, peptides, nutraceuticals, anti-obesity agents, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasympathomimetics, parathyroid, calcitonin, biphosphonates, prostaglandins, radio-pharmaceuticals, sex hormones, anti-allergic agents, stimulants and anoretics, sympathomimetics, thyroid agents, vasodilators, xanthines, acne medication, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

20. The composition of claim 19, wherein the nutraceutical is selected from the group consisting of dietary supplements, vitamins, minerals, herbs, healing foods that have medical or pharmaceutical effects on the body, folic acid, fatty acids, fruit and vegetable extracts, vitamin supplements, mineral supplements, phosphatidylserine, lipoic acid, melatonin, glucosamine/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish and marine animal oils, and probiotics.

21. The composition of claim 1, wherein the active agent is selected from the group consisting of acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfioxacin, olanzapine, omeprazole, penciclovir, pimozide, tacolimus, quazepam, raloxifene, rifabutin, rifampin, risperidone, rizatriptan, saquinavir, sertraline, sildenafil, acetylsulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

22. The composition of claim 1, wherein the active agent is selected from the group consisting of an analgesic, ketoprofen, and naproxen.

23. The composition of claim 1, comprising at least two surface stabilizers.

24. The composition of claim 1, wherein the surface stabilizer is selected from the group consisting of an ionic surface stabilizer, an anionic surface stabilizer, a cationic surface stabilizer, a nonionic surface stabilizer, and a zwitterionic surface stabilizer.

25. The composition of claim 1, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methyl-glucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-phospholipid, PEG-cholesterol, PEG-cholesterol derivative, PEG-vitamin A, and random copolymers of vinyl acetate and vinyl pyrrolidone.

26. The composition of claim 24, wherein the at least one cationic surface stabilizer is selected from the group consisting of a polymer, a biopolymer, a polysaccharide, a cellulosic, an alginate, a nonpolymeric compound, a phospholipid, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$) dimethyl-benzyl ammonium chloride, N-tetradecyldimethyl-benzyl ammonium chloride monohydrate, dimethyl dodecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-dodecyldimethyl ammonium chloride, N-tetradecyldimethylbenzyl ammonium, chloride monohydrate, N-alkyl ($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethyl ammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquatemium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quatemized polyoxyethylalkylamines, quatemized ammonium salts polymers, alkyl pyridinium salts; amines, amine salts, amine oxides, imide azolinium salts, protonated quatemary acrylamides, methylated quatemary polymers, and cationic guar.

27. The composition of any of claims 24 or 26, wherein the composition is bioadhesive.

28. The composition of claim 1, wherein the time to $T_{max}$ of the active agent, when assayed in the plasma of a mammalian subject following administration, is less than the time to $T_{max}$ for a non-nanoparticulate form of the same active agent, administered at the same dosage.

29. The composition of claim 28, wherein the time to $T_{max}$ is selected from the group consisting of not greater than about 90%, not greater than about 80%, not greater than about 70%, not greater than about 60%, not greater than about 50%, not greater than about 30%, not greater than about 25%, not greater than about 20%, not greater than about 15%, and not greater than about 10% of the time to $T_{max}$, exhibited by a non-nanoparticulate formulation of the same active agent, administered at the same dosage.

30. The composition of claim 1, wherein the $C_{max}$ of the active agent, when assayed in the plasma of a mammalian subject following administration, is greater than the $C_{max}$ for a non-nanoparticulate form of the same active agent, administered at the same dosage.

31. The composition of claim 30, wherein the $C_{max}$ is selected from the group consisting of at least about 10%, at least about 20%, at least about 30%, at least about 40%, at least about 50%, at least about 60%, at least about 70%, at least about 80%, at least about 90%, and at least about 100% greater than the $C_{max}$ exhibited by a non-nanoparticulate formulation of the same active agent, administered at the same dosage.

32. The composition of claim 1, wherein the AUC of the active agent, when assayed in the plasma of a mammalian subject following administration, is greater than the AUC for a conventional, non-nanoparticulate form of the same active agent, administered at the same dosage.

33. The composition of claim 32, wherein the AUC is selected from the group consisting of at least about 10%, at least about 20%, at least about 30%, at least about 40%, at least about 50%, at least about 60%, at least about 70%, at least about 80%, at least about 90%, and at least about 100% greater than the AUC exhibited by a non-nanoparticulate formulation of the same active agent, administered at the same dosage.

34. The composition of claim 1 which does not produce significantly different absorption levels when administered under fed as compared to fasting conditions.

35. The composition of claim 34, wherein the difference in absorption of the active agent composition of the invention, when administered in the fed versus the fasted state, is selected from the group consisting of less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, and less than about 3%.

36. The composition of claim 1, wherein administration of the composition to a subject in a fasted state is bioequivalent to administration of the composition to a subject in a fed state, when administered to a human.

37. The composition of claim 36, wherein "bioequivalency" is established by a 90% Confidence Interval of between 0.80 and 1.25 for both $C_{max}$ and AUC, when administered to a human.

38. The composition of claim 36, wherein "bioequivalency" is established by a 90% Confidence Interval of between 0.80 and 1.25 for AUC and a 90% Confidence Interval of between 0.70 to 1.43 for $C_{max}$, when administered to a human.

39. The composition of claim 1, wherein upon administration the composition redisperses such that the active agent particles have an effective average particle size selected from the group consisting of less than about 2000 nm, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

40. The composition of claim 1, wherein the composition redisperses in a biorelevant media such that the active agent particles have an effective average particle size selected from the group consisting of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

41. A solid or semi-solid gelatin pharmaceutical composition comprising:
    (a) particles of at least one active agent having an effective average particle size of less than about 2000 nm prior to inclusion in the solid or semi-solid gelatin pharmaceutical composition;
    (b) at least one surface stabilizer adsorbed on the surface of the particles; and
    (c) a gel matrix of at least one gel forming substance, the gel forming substance in an amount which exhibits gelation sufficient to retain water in an amount of from about 45% to about 90% based on the total weight of the composition,
    wherein the nanoparticulate active agent particles with the adsorbed surface stabilizer are dispersed in the gel matrix,
    wherein the composition is made by a process comprising the steps:
        (i) heating the at least one gel forming substance to form a molten composition;
        (ii) adding the particles of at least one active agent and at least one surface stabilizer to the molten gel forming substance composition;
        (iii) mixing the composition resulting from combining (i) and (ii); and
    (iv) refrigerating the composition of step (iii) until a solid or semi-solid pharmaceutical composition is obtained.

42. A method of preparing a homogenous solid or semi-solid gelatin composition comprising:
    (a) combining:
        (i) a nanoparticulate active agent composition comprising particles of at least one active agent and at least one surface stabilizer adsorbed on the surface of the particle, wherein the active agent particles have an effective average particle size of less than about 2000 nm, and
        (ii) at least one gel forming substance selected from the group consisting of a natural gelatin, a semi-synthetic gelatin, and a synthetic gelatin in an amount which exhibits gelation sufficient to retain the water in a solid or semi-solid form, to form a solid or semi-solid dose matrix surrounding the nanoparticulate active agent composition; and (b) forming a solid dose formulation wherein the nanoparticulate active agent particles with the adsorbed surface stabilizer are homogenously dispersed throughout the gel matrix, wherein such formation does not comprise solubilizing the at least one active agent, and wherein the solid or semi-solid dosage formulation comprises from about 45% to about 90% water, based on the total weight of the composition.

43. A method of treating a subject comprising administering to the subject an effective amount of a homogenous solid or semi-solid gelatin formulation, wherein the formulation comprises:

(a) particles of at least one active agent having an effective average particle size of less than about 2000 nm prior to inclusion in the dosage form;

(b) at least one surface stabilizer adsorbed on the surface of the particle; and (c) at least one gel forming substance selected from the group consisting of a natural gelatin, a semi-synthetic gelatin, and a synthetic gelatin in an amount which exhibits gelation sufficient to retain the water in a solid or semi-solid state, wherein the gel forming substance forms a matrix surrounding the nanoparticulate active agent particles and surface stabilizer, wherein the nanoparticulate active agent particles with the adsorbed surface stabilizer are homogenously dispersed throughout the gel matrix, and wherein the formulation comprises from about 45% to about 90% water, based on the total weight of the composition.

44. The method of claim 43, wherein the subject is fasted prior to administration.

* * * * *